United States Patent [19]

Hunter et al.

[11] Patent Number: 5,565,185
[45] Date of Patent: Oct. 15, 1996

[54] PROCESS FOR THE PREPARATION OF RADIOLABELED META-HALOBENZYLGUANIDINE

[75] Inventors: Duncan H. Hunter, London; Alok Goel, Etobicoke; Richard J. Flanagan, St. Lazare, all of Canada

[73] Assignee: Merck Frosst Canada, Inc., Kirkland, Canada

[21] Appl. No.: 277,809

[22] Filed: Jul. 20, 1994

[51] Int. Cl.$^6$ .......................... A61K 51/04; C07C 277/00
[52] U.S. Cl. .......................... 424/1.85; 564/237; 564/238
[58] Field of Search .......................... 424/1.85; 564/237, 564/238

[56] References Cited

U.S. PATENT DOCUMENTS

| | | | |
|---|---|---|---|
| 4,584,187 | 4/1986 | Wieland et al. | 424/1.85 |
| 5,413,779 | 5/1995 | Kuhar et al. | 424/1.85 |

OTHER PUBLICATIONS

Sexton et al., Soc. Neurosci. Abstr. 17(1–2) (1991).
Wafelman et al., "Synthesis, Radiolabeling and Stability of Radioiodirated m–Iodobenzylguanidine, a Review", Appl. Radiat. Isot., vol. 45, No. 10 pp. 997–1007, (1994).
Vaidyanathan et al., Appl. Radiat. Isot., vol. 44, No. 3, pp. 621–628 (1993).
Weiland et al., J. Nucl. Med., vol. 21, No. 4, pp. 349–353 (1980).
Mangner et al., J. Org. Chem., vol. 47, pp. 1484–1488 (1982).
The Lancet, pp. 905–907 (1984).

*Primary Examiner*—Gary E. Hollinden
*Assistant Examiner*—Michael G. Hartley
*Attorney, Agent, or Firm*—J. Eric Thies; David L. Rose

[57] ABSTRACT

The present invention provides a no-carrier-added synthesis of radiolabeled meta-halobenzylguanidine by halodestannylation which comprises reacting a meta-trialkylstannylbenzylguanidine with a source of radionuclide of a halogen. The present invention also provides meta-trialkylstannylbenzylguanidine as intermediates in the afore-mentioned process.

8 Claims, No Drawings

PROCESS FOR THE PREPARATION OF RADIOLABELED META-HALOBENZYLGUANIDINE

BACKGROUND OF THE INVENTION

The present invention relates to a process for the preparation of radiolabeled meta-halobenzylguanidine, as well as intermediate compounds used in this process.

Radiohalogenated meta-iodobenzylguanidine is an agent useful for imaging the adrenal medulla and its associated neoplasms. Specifically, the compound $^{131}$I-meta-iodobenzylguanidine ($^{131}$I-MIBG) is currently being used for the diagnosis and localization of primary and metastatic pheochromocytomas, neuroblastomas, medullary thyroid carcinomas, paragangliomas, carcinoid ramors and apudomas. $^{131}$I-MIBG is also being evaluated in the therapy of neuroendocrine malignancies, such as carcinoid tumors, pheochromocytomas, and neuroblastomas.

Currently, $^{131}$I-MIBG is prepared by an isotopic exchange method using meta-iodobenzylguanidine (MIBG) and a source of radioiodide. Because isotopic exchange is an equilibrium process the product obtained thereby necessarily contains a significant amount of the carder MIBG and results in product preparations having specific activities generally in the order of 100 Ci/mmol. The administration of a typical 5 mCi dose of $^{131}$I-MIBG made by the isotopic exchange process would result in the co-administration of about 5 mg of MIBG. This amount of MIBG received by the patient may cause unwanted pharmacological effects and is a particular concern in children because of their smaller body weight. Thus, no-carder-added synthesis of $^{131}$I-MIBG would be desirable to circumvent potential problems that may be associated with carder presence.

Vaidyanathan and Zalutsky (*Appl. Radiat. Isot.*, 44(3):621–628, 1993) attempted unsuccessfully to synthesize 3-(tri-n-butylstannyl)benzylquanidine, a compound that would have allowed the introduction of the radioiodine label by iododestannylation as the last step in the synthesis of $^{131}$I-MIBG. Instead, $_{131}$I3-iodobenzylamine was prepared and then converted to $^{131}$I-MIBG with cyanamide; this process has the disadvantage that radioiodine is introduced in the penultimate step of the synthesis rather than in the last step. Vaidyanathan and Zalutsky also reported the synthesis of $^{131}$I-MIBG by iododesilylation of 3-trimethylsilylbenzylguanidine; however, the synthesis of 3-trimethylsilylbenzylguanidine requires multiple steps and is therefore not suitable for large scale production of $^{131}$I-MBG. Thus, there still exists the need for an efficient and practical non-carder-added synthesis of $^{131}$I-MIBG.

SUMMARY OF THE INVENTION

The present invention provides an efficient and practical no-carder-added synthesis of radiolabeled meta-halobenzylguanidine by halodestannylation. The material obtained from the process of the present invention routinely attains specific activity of approximately 2,000 Ci/mmol; thus, the administration of a typical 5 mCi dose of $^{131}$I-MIBG prepared by the present process would result in the administration of only about 2.5 μg of the carder MIBG.

The present invention also provides the intermediate compounds 3-trialkylstannylbenzylguanidine.

DETAILED DESCRIPTION OF THE INVENTION

The present invention provides a process for the preparation of a compound of the formula (I)

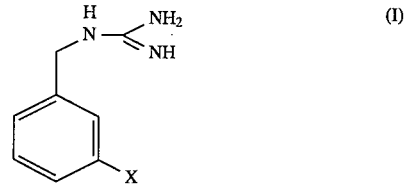

wherein X is a radionuclide of a halogen, which comprises: reacting a meta-trialkylstannylbenzylguanidine of the formula (II)

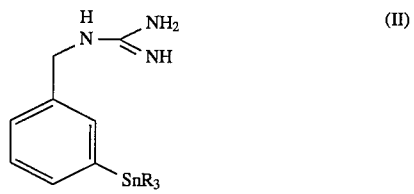

wherein R is an alkyl group having from 1 to 4 carbon atoms, or an acid addition salt thereof, with a radiohalogen in the presence of an oxidant.

In a preferred embodiment, the process is carded out in a polar protic organic solvent, and under acidic condition.

In a second preferred embodiment, the R of a compound of formula (II) is an alkyl group having from 1 to 3 carbon atoms; more preferably R is methyl.

In a third preferred embodiment, the source of radionuclide of a halogen is a Group IA metal salt of a radioiodide; more preferably it is sodium $^{131}$I.

In a more preferred embodiment there is provided a process for the preparation of $^{131}$I-MIBG which comprises: reacting a compound of formula (II) wherein R is methyl, with a Group IA metal salt of 131 I, in the presence of a peracid oxidizing agent, in a polar protic organic solvent under acidic condition.

Another aspect of the present invention provides a compound having the formula (II)

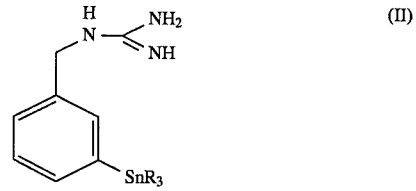

wherein R is an alkyl group having from 1 to 4 carbon atoms; or an acid addition salt thereof: In a preferred embodiment of the compound of formula (II), R is methyl.

Unless specifically stated otherwise, the following definitions and abbreviations are applicable throughout the application.

"Alkyl" includes straight and branched saturated carbon chains. Examples include methyl, ethyl, n-propyl, isopropyl, n-butyl, sec-butyl, and t-butyl.

"Halogen" includes fluorine, chlorine, bromine and iodine.

"Iodobeads®" is polystyrene immobilized chloramine-T marketed by Pierce Chemical Co., Rockford, Ill.

"Radiohalogen" means a halogen nuclide capable of undergoing radioactive decay.

"THF" is tetrahydrofuran.

The process of the present invention is exemplified below in Scheme I.

SCHEME I

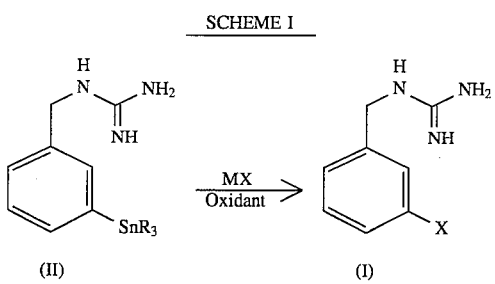

In Scheme I, R is an alkyl group having from 1 to 4 carbon atoms; an alkyl group having from 1 to 3 carbon atoms is preferred, with methyl being the more preferred.

X is a radionuclide of a halogen; examples of X include radioiodines $^{123}I$, $^{124}I$, $^{125}I$, and $^{131}I$, and radiobromines $^{77}Br$, $^{78}Br$, $^{80}Br$, and $^{82}Br$ also $^{75}Br$ and $^{211}At$. A radioiodine is preferred, with $^{131}I$ being the more preferred.

M is a metal cation selected from Group IA and Group IIA metals; examples of M include lithium, sodium, potassium, magnesium, and calcium. Preferred M is a Group IA metal, with sodium being the more preferred.

As depicted in Scheme 1 a trialkystannylbenzylguanidine of formula (II) is treated with a source of radionuclide of a halogen such as a Group IA or Group IIA metal salt of a radiohalide, MX, in the presence of an oxidant. Suitable MX salts are those that are soluble in the reaction medium, and may be for example $Na^{123}I$, $Na^{124}I$, $K^{125}I$, $Na^{131}I$, $Mg(^{77}Br)_2$, $K^{78}Br$, $Na^{80}Br$, and the like. It is to be understood that the source of radionuclide is not limited to MX but may also be for example?

The oxidant may be any that facilitates the halodestannylation reaction. Suitable oxidants are for example N-chloro oxidizing agents such as chloramine-T, dichloramine-T, chloramine-B, 1,3,4,6-tetrachloro- 3α,6α-diphenylglycoluril and the like; and peracids such as peracetic acid, perbenzoic acid, and the like. The preferred oxidant is peracetic acid.

The halodestannylation reaction is carded out at a temperature conducive to the formation of the desired product, for example in the range of 0° to 30° C. but typically at room temperature. The reaction is conducted preferably in a polar protic organic solvent; suitable solvents are for example alkanols having up to four carbon atoms such as methanol, ethanol, isopropanol and the like. The preferred solvent is methanol. The reaction medium is preferably maintained at pH 7 ranging from 5.5 to 7.5 with the addition of an acid such as an alkanoic acid containing up to six carbon atoms; suitable acids are for example formic, acetic, propanoic, oxalic, glycolic, butanoic, 2-methylpropanoic, tartaric, trifluoroacetic acids, and the like.

Compounds of formula (I) thus obtained may be recovered using techniques well known in the art. For example, column chromatography using silica gel along with appropriate eluants as organic solvents may be used to effectively purified the desired compound.

The starting material used in the present process, i.e. compounds of formula (II) may be prepared by the process depicted in Scheme II.

SCHEME II

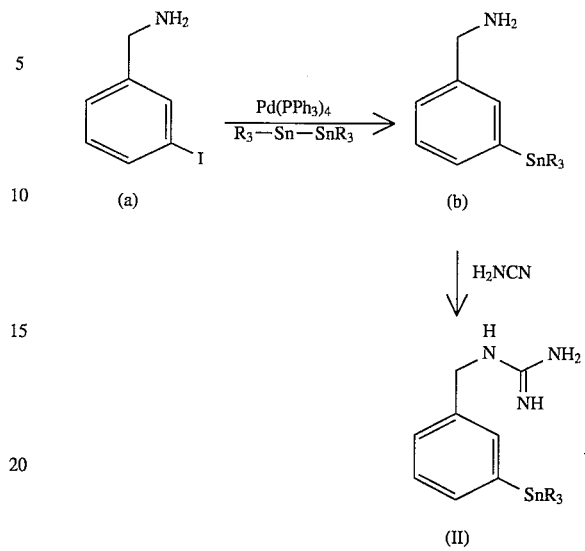

Commercially available 3-iodobenzylamine hydrochloride is first converted to the amine base (a) by treatment with a base such as ammonium hydroxide. In the first step of Scheme II, compound (a) is converted to the corresponding trialkylstannyl compound (b) using hexaalkylditin and a catalytic amount of tetrakis(triphenylphosphine)Pd(O). This reaction is carded out under inert atmosphere (e.g. under argon) in an inert organic solvent such as aromatic hydrocarbons, for example toluene, and at elevated temperature, for example around 70° C. The reaction is generally complete within about 24 hours. Crude compound (b) may be purified by crystallization, for example from ether:hexanes, for use in the subsequent step.

Compound (b) is treated with cyanamide ($H_2NCN$) to produce the corresponding compound (II). The reaction is conducted in an inert organic solvent such as tetrahydrofuran and at an elevated temperature, e.g. at about 50° C., and is usually complete within about 24 hours.

The $^{131}I$-MIBG preparation obtained by this inventive process is used in the same manner as that of the prior art, i.e. will the formulation, dosage, regimen as described in the prior art.

The following examples are provided to further illustrate the invention and are not to be construed as limiting the invention in any manner.

Preparation I: 3-Trimethyltin benzylamine

To a stirred solution of 3-iodobenzylamine hydrochloride dissolved in distilled water (13.2 mL per gram) is added dropwise an aqueous ammonium hydroxide (5.3 mL per gram) solution. A yellow oil separates and is extracted into ethyl acetate (3×6.6 mL per gram). The ethyl acetate layer is dried over anhydrous sodium sulfate and evaporated on a rotovap to obtain 3-iodobenzylamine as a yellow oil (94% yield).

Tetrakis(triphenylphosphine) palladium (0) catalyst (0.013 eq.) is added to a solution of 3-iodobenzylamine (1 eq.) and hexamethyl ditin (1.07 eq.) in toluene (6 mL per g of the amine), and stirred at 70° C. for 17 h, under an argon atmosphere. The reaction mixture turns black. The mixture is cooled to room temperature and the toluene is removed under vacuum at 50° C. to obtain a black residue. Ethyl acetate (61.3 mL per g of the amine) is added to the residue, stirred, and filtered through a sintered glass funnel (pore size 4.0–5.0) to obtain a yellow solution. This solution is washed with brine (3X), dried over anhydrous sodium sulfate, and evaporated to obtain crude title compound (85% yield). Crystallization of the crude product from ether:hexanes (2:1 v/v, 53.6 mL per gram) affords white crystals of 3-trimethyltin benzylamine (83% yield). Recrystallization from hot ether-hexanes (1:2 v/v, 30 mL per g) affords pure 3-trimethyltin benzylamine as a white crystalline solid (mp 78° C., 53% yield).

Preparation II: 3-Trimethyltin benzylguanidine

Dilute hydrochloric acid solution (0.1M, 0.05 eq.) is added to a solution of 3-trimethyltin benzylamine (1 eq.) in distilled tetrahydrofuran (10 mL per g of the amine). After the solution is stirred for 5 min. at room temperature, cyanamide (1.5 eq.) is added, and the mixture is stirred at 50° C. for 24 h. The mixture is cooled to room temperature, and the THF is evaporated on a rotovap. Traces of solvent are evaporated with a vacuum pump to obtain a yellow oil. The oil is taken up in methanol, filtered through a cotton plug, and the methanol is evaporated to obtain pure 3-trimethyltin benzylguanidine (m/e 313).

EXAMPLE 1

$^{131}$I-MIBG

Acetic acid (0.01 mL) is added to a mixture of 3-trimethyltin benzylguanidine (5–10 micrograms in 0.02 mL of methanol) and Na$^{131}$I solution (0.250 mCi, 0.01 mL). Two Iodobeads® are added and the mixture is shaken. It is then diluted with distilled water (0.1 mL) and passed through a silica gel sep-pak column (100 mg; preconditioned with methanol). The column is eluted with THF-0.1 M sodium dihydrogenphosphate buffer (0.1 mL, 1:4 v/v), and the eluate is discarded. Finally, column is eluted with THF (0.2 mL) to obtain no-carrier-added $^{131}$I-MIBG (24 % yield).

EXAMPLE 2

Water (100 L) is added to a mixture of 3-trimethyltin benzylguanidine (5–10 grams in 20 μL of methanol) and Na$^{131}$I solution (10–20 mCi, 100 mL). Peracetic acid (10 μL of 3.2% solution in 10% acetic acid in water) is added and the mixture is allowed to react for one minute. Excess oxidizing agent is destroyed with excess sodium thiosulfate.

The crude reaction mixture is injected directly onto a C-18 reverse phase MPLC column and the desired product eluted with a mixture of water/acetonitrile containing 0.1% trifluoroacetic acid.

What is claimed is:

1. A process for the preparation of a compound of the formula (I)

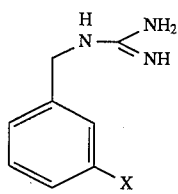

wherein X is a radionuclide of a halogen, which comprises: contacting a meta-trialkylstannylbenzylguanidine of the formula (II)

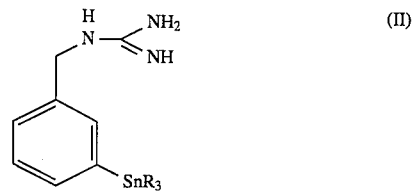

wherein R is an alkyl group having from 1 to 4 carbon atoms, or an acid addition salt thereof, with a source of radionuclide of a halogen in the presence of an oxidant.

2. A process of claim 1 wherein R is methyl.

3. A process of claim 1 wherein the source of radionuclide of a halogen is a Group IA metal salt of a radioiodide.

4. A process of claim 1 wherein said process is carried out in a polar organic solvent, and under acidic condition.

5. A process for the preparation of $^{131}$I-MIBG which comprises: contacting a compound of formula (II)

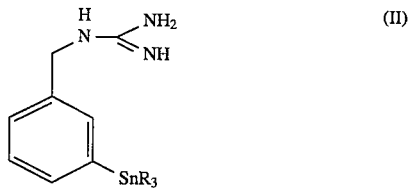

wherein R is methyl, with a Group IA metal salt of $^{131}$I, in the presence of an N-chloroamide oxidizing agent, in a polar organic solvent under acidic condition.

6. A process of claim 5 wherein said metal is sodium, and said oxidizing agent is chloramine-T.

7. A compound having the formula (II)

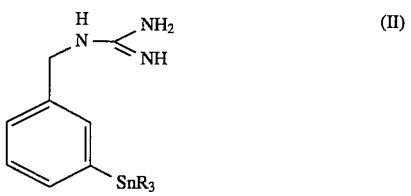

wherein R is an alkyl group having from 1 to 4 carbon atoms; or an acid addition salt thereof.

8. A compound of claim 7 wherein R is methyl.

* * * * *